US005837467A

United States Patent [19]
Kaempfer et al.

[11] Patent Number: 5,837,467
[45] Date of Patent: Nov. 17, 1998

[54] METHOD FOR PREDICTING THE RESPONSE TO TREATMENT WITH BCG OF SUPERFICIAL BLADDER CARCINOMA

[75] Inventors: Raymond Kaempfer, Jerusalem; Amos Shapiro, Mevaseret Ziyon, both of Israel

[73] Assignees: Yissum Research Development Company of the Hebrew University of Jerusalem; Hadasit Medical Research Services and Development Company Ltd., both of Jerusalem, Israel

[21] Appl. No.: 786,503

[22] Filed: Jan. 21, 1997

[51] Int. Cl.$^6$ ............................. G01N 33/574; C12Q 1/68
[52] U.S. Cl. ............................. 435/6; 435/7.23; 435/7.24; 435/385; 436/63; 436/64
[58] Field of Search ............................. 435/6, 7.23, 7.24, 435/385; 436/63, 64

[56] References Cited

FOREIGN PATENT DOCUMENTS 0309558  11/1994  European Pat. Off. .

OTHER PUBLICATIONS

Arad et al., (1995) "Transient Expression of Human Interleukin–2 and Interferon–γ Genes Is Regulated by Interaction Between Distinct . . . " *Cell Immunol.*, 160:240–247.
Bancroft et al., (1989) "Tumor Necrosis Factor Is Involved In The T Cell–Independent Pathway Of Macrophage Activation In scid Mice" *J. Immunol.*, 143:127–130.
Bancroft and Schreiber (1992) "Natural Immunity: A T–Cell–Independent Pathway Of Macrophage Activation Defined In The acid Mouse" *Immunol. Rev.*, 124:5–24.
Boccafoschi et al., (1992) "Immunophenotypic Characterization of the Bladder Mucosa Infiltrating Lymphocytes After Intravesical BCG . . . " *Eur Urol.*, 21:304–308.
Bohle et al., (1991) "Effects Of Local Bacillus Calmette–Guerin Therapy In Patients With Bladder Carcinoma On Immunocompetent . . . " *J. Urol.*, 144:53–58.
Bohle et al., (1991) "Elevations Of Cytokines Interleukin–1, Interleukin–2, And Tumor Necrosis Factor In The Urine Of Patients . . . " *J. Urology*, 144:59–64.
Bohle et al., (1992) "Long–term–Immunobiological Effects Of Intravesical Bacillus Calmette–Guerin Against Bladder Carcinoma . . . " *Dev Biol Stand.*, 77:199–209.
Bretton et al., (1990) "The Response of Patients With Superficial Bladder Cancer To A Second Course Of Intravesical Bacillus . . . " *J. Urol.*, 143:710–712.
Kronke et al., (1985) "Sequential Expression Of Genes Involved In Human T Lymphocyte Growth And Differentiation" J. Exp. Med. 161: 1593–1598.
Brosman (1982b) "Experience With Bacillus Calmette–Guerin In Patients With Superficial Bladder Carcinoma" *J. Urol.*, 128:27–30.
Bubenik et al., (1988) "Defect In Lectin–Induced Interleukin 2 Production By Peripheral Blood Lymphocytes Of Patients With . . . " *Immunol Lett.*, 18:115–118.

Cheley et al., (1984) "A Reproducible Microanalytical Method For The Detection Of Specific RNA Sequences by Dot–Blot Hybridization" *Anal Biochem.*, 137:15–19.
Connor et al., (1993) "Regressoin Of Bladder Tumors In MIce Treated With Interleukin 2 Gene–Modified Tumor Cells" *J. Exp. Med.*, 177:1127–1134.
Coplen et al., (1990) "Long–Term Followup OF Patients Treated With 1 or 2, 6–Week Courses Of Intravesical Bacillus Calmette–Guerin: . . . " *J. Urol.*, 144:652–657.
De Jong et al., (1990) "Presence Of Interleukin–2 In Urine Of Superficial Bladder Cancer Patients After Intravesical Treatment . . . " *Cancer Immunol. Immunother*, 31:182–186.
Efrat et al., (1982) Kinetics Of Induction And Molecular Size of mRNAs Encoding Human Interleukin–2 and γ–Interferon Nature, 297:236–239.
Efrat et al., (1984a) "Control Of Biologically Active Interleukin 2 Messenger RNA Formation In Induced Human Lymphocytes" Proc Natl Acad Sci USA, 81:2601–2605.
Efrat et al., (1984b) "Superinduction of Human Interleukin–2 Messenger RNA By Inhibitors Of Translation" Biochem Biphys Res Commun., 123:842–848.
Gerez et al., (1991a) "Aberrant Regulation of Interleukin–2 but Not of Interfection–γ Gene Expression in Down Syndrome (Trisomy 21)" Clin Immunol Immunopathol., 58:251–266.
Gerez et al., (1991b) "Regulation of Interleukin–2 And Interferon–γ Gene Expression In Renal Failure" Kidney Int., 40:266–272.
Gerez et al., (1995) "Post–transcriptional Regulation of Human Interleukin–2 Gene Expression At Processing Of Precursor Transcripts" J. Biol. Chem., 270:19569–19575.

(List continued on next page.)

Primary Examiner—Toni R. Scheiner
Attorney, Agent, or Firm—Kohn & Associates

[57] ABSTRACT

The invention relates to a method and kit for the prediction of the response of a patient suffering from superficial bladder carcinoma to treatment with bacillus Calmette-Guérin (BCG), by calculating the inducibility of the Interleukin-2 (IL-2) gene of the patient in a sample of peripheral blood mononuclear (PBM) cells from the patient receiving BCG. The method includes the steps of culturing at least two aliquots of PBM from the patient where the cells in a first aliquot are cultured in the presence of an inducing agent for inducing expression of the IL-2 gene and the cells in the second aliquot are cultured in the absence of the inducing agent. The extent of expression of the IL-2 gene is quantitatively determined for each aliquot. The ratio of the extent of the expression of the IL-2 gene in the first aliquot to the extent of the expression of the IL-2 gene in the second aliquot is calculated, the ratio providing a measure of the inducibility of the IL-2 gene. The inducibility is in a direct relationship with the probability of entering remission, relapse or persistence of bladder carcinoma in the patient. Patients with a ratio below about 1.5 can be treated either with a cytokine preparation, a second course of treatment with the BCG or a second course of treatment with the BCG in combination with a cytokine preparation to improve response.

15 Claims, 6 Drawing Sheets

OTHER PUBLICATIONS

Fleischman et al., (1989) "Urinary Interleukins In Patients Receiving Intravescular Bacillus Calmette–Guerin Therapy For Superficial . . . " Cancer, 64:1447–1454.

Herr et al., (1983) "Effect Of Intravesical Baciluus Calmette–Guerin (BCG) on Carcinoma In Situ Of The Bladder" Cancer, 51:1323–1326.

Ikemoto et al., (1990) "Clinical Studies on Cell–Mediated Immunity In Patients With Urinary Bladder Carcinoma: Blastogenic Response . . . " Br. J. Urol., 65:333–338.

Kaempfer et al., (1996) "Prediction of response to treatment in superficial bladder carcinoma through pattern of Interleukin–2 . . . " J. Clin. Oncology, 14:1778–1786.

Lamm et al., (1980a) "Bacillus Calmette–Guerin Immunotherapy of Of Superficial Bladder Cancer" Cancer, 48:82–88.

Lamm et al., (1980b) "BCG Immunotherapy Of Bladder Cancer: Inhibition Of Tumor Recurrence and Associated Immune Response" J. Urol., 124:38–42.

Lebendiker et al., (1987) "Superinduction Of The Human Gene Encoding Immune Interferon" EMBO J., 6:585–589.

Mosmann et al., (1986) "Two Types Of Murine Helper T Cell Clone" J. Immunol., 136:2348–2357.

Mosmann et al., (1989) "TH1 And TH2 Cells: Different Patterns Of Lymphokine Secretion Lead To Different Functional Properties" Annu Rev Immunol., 7:145–173.

Ratliff et al., (1993) "T–Cell Subsets Required For Intervesical BCG Immunotherapy For Bladder Cancer" J. Urol., 150:1018–1023.

Shapiro et al., (1982) "Immunotherapy Of Superficial Bladder Cancer" J. Urol., 128:891–894.

Shaw et al., (1987) "Induction, Suppression And Superinduction Of Lymphokine mRNA In T Lymphocytes*" Mol. Immunol., 24:409–419.

Shaw et al., (1988) "Mechanisms Regulating The Level Of IL–2 mRNA In T Lymphocytes" J. Immunol., 140:2245–2248.

Silverberg et al., (1989) "Cancer Statistics, 1989" J. A. CA Cancer J. Clin. 39:3–20.

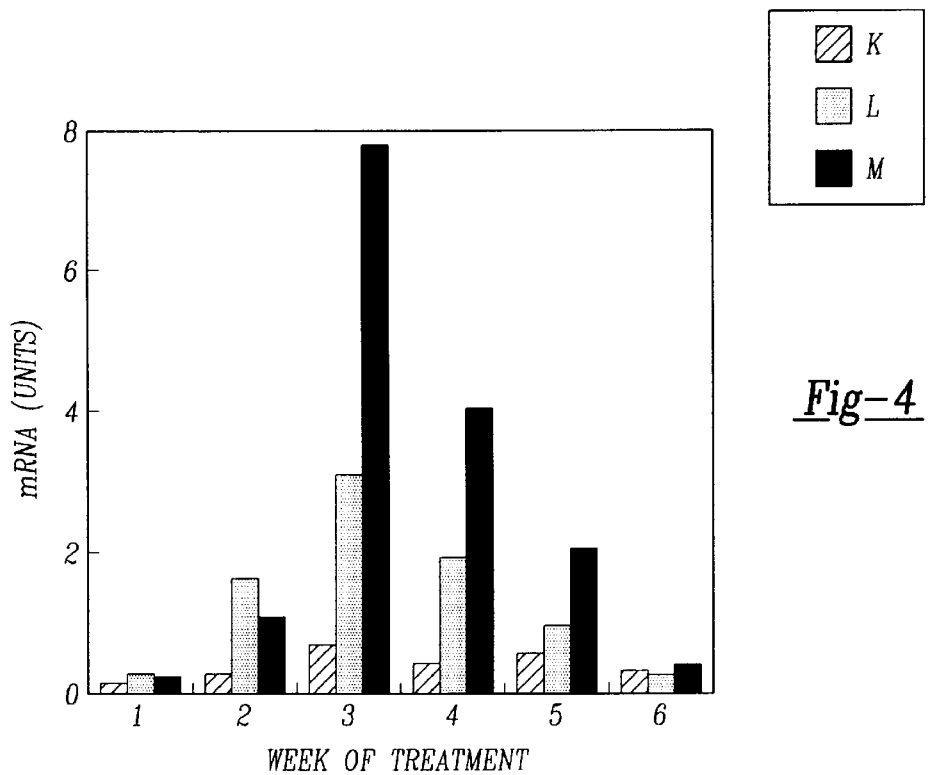
Fig-4
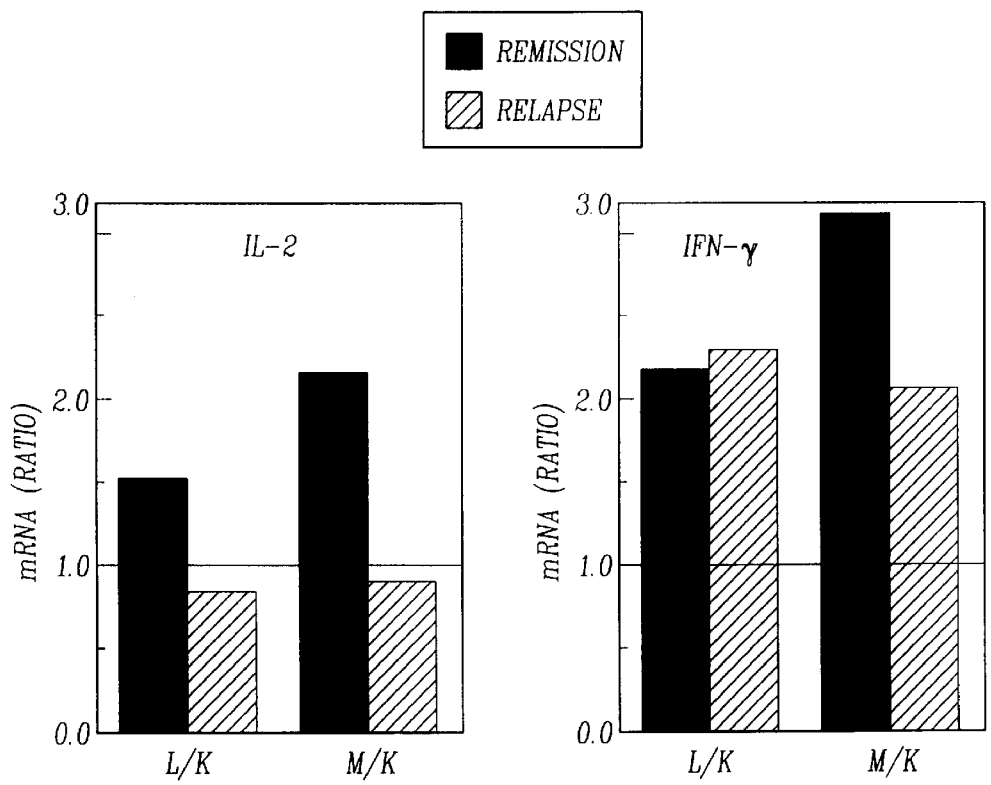
Fig-5A
Fig-5B

METHOD FOR PREDICTING THE RESPONSE TO TREATMENT WITH BCG OF SUPERFICIAL BLADDER CARCINOMA

BACKGROUND OF THE INVENTION

1. Technical Field

The invention relates to a method for predicting the response of a patient suffering from superficial bladder carcinoma to treatment with BCG and to methods of improving the treatment of superficial bladder carcinoma.

2. Background Art

Carcinoma of the bladder is the fifth most common form of cancer [Silverberg, et al. (1993)]. Most tumors are superficial. Papillary tumors are treated by trans-urethral resection and local therapy, for which intravesical administration of bacillus Calmette-Guérin (BCG) is by far the most effective [Herr, et al. (1983); Lamm, et al. (1980a); Brosman, (1982a)]. Carcinoma in situ (CIS) is treated solely with BCG. This treatment has a remission rate approaching 70% [Herr, et al. (1983); Lamm, et al. (1980a); Brosman, (1982a)]. Approximately one third of patients fail to respond, suffering relapse or persistence of the tumor. In terms of dose and duration, BCG treatment is largely empirical. Its adjustment to the individual patient has been prevented by the lack of predictive parameters. A second course of BCG is administered once recurrence or persistence of the tumor is detected [Bretton, et al. (1990); Coplen, et al. (1990)]. Despite these limitations, treatment of superficial bladder carcinoma with BCG represents a model for immunotherapy of cancer [Ratliff, et al. (1993)].

BCG is believed to activate the cellular immune response, which is impaired in urinary bladder carcinoma as reflected by a diminished blastogenic response and decreased production of interleukin-2 (IL-2) and interferon-γ (IFN-γ) [Bubenik, et al. (1988); Ikemoto, et al. (1990)]. Following local administration of BCG, a persistent increase in mononuclear cells, predominantly CD4-positive helper T cells, has been observed in the bladder, leading to an elevated CD4/CD8 ratio [Bohle, et al. (1990a); Bohle, et al. (1992); Boccafoschi, et al. (1992)]. This increase was, however, independent of response to treatment [Boccafoschi et al. (1992)]. Treatment with BCG induces local production of cytokines in the bladder [Bohle et al. (1992)] and the prompt appearance of IL-1, IL-2 and tumor necrosis factor-a in the urine [Bohle et al. (1990a); De Jong, et al. (1990); Fleischman, et al. (1989); Bohle, et al. (1990b)]. No correlation has been detected between levels of secreted cytokines and response to treatment [Bohle, et al. (1990b); De Jong (1990); Fleischman (1989); Bohle et al. (1990a)].

Since, as stated above, approximately one third of patients suffering from superficial bladder carcinoma treated with BCG fail to respond and suffer relapse or persistence of the tumor, there exists a need for a diagnostic tool which would enable the prediction of the response to treatment with BCG of superficial bladder carcinoma, in order to apply repetitive, alternative or complementary therapy and improve the prospects of remission. The various attempts described above did not provide any such tool.

Induction of IL-2 and IFN-γ gene expression in peripheral blood mononuclear cells (PBMC) or tonsil cells from healthy human donors yields a transient wave of mRNA [Efrat, et al. (1982); Efrat, et al. (1984a); Lebendiker, et al. (1987)]. The amplitude of this mRNA wave can be superinduced by inhibitors of translation, [Efrat, et al. (1984a); Lebendiker, et al. (1987); Efrat, et al. (1984b); Gerez, et al. (1995); Shaw, et al. (1988); Shaw, et al. (1987)] without any increase in primary transcription [Gerez, et al. (1995); Kronke, et al. (1985)]. Besides extensive reduction of the mRNA signal through this post-transcriptional mechanism, expression of IL-2 and IFN-γ genes is sensitive to cell-mediated suppression and is superinduced tenfold upon depletion of CD8 cells [Arad, et al. (1995)]. These control mechanisms ensure that IL-2 and IFN-γ genes are normally expressed to only a small proportion of their full potential and render their expression particularly sensitive to regulation by external signals. These findings could serve as a basis in the search for a diagnostic tool for predicting the response to treatment of superficial bladder carcinoma with BCG.

EP 0 309 558 discloses a method for calculating the inducibility of bioregulatory genes such as IL-2 and IFN-γ. However, this publication provides no insight into the question whether in peripheral blood mononuclear cells from a patient with superficial bladder carcinoma, expression of the IL-2 gene is normal or abnormal and if abnormal, what, if any, is the relationship of such abnormal expression to clinical outcome defined as remission, relapse or persistence of the tumor. Moreover, this publication refers to determining the inductivity of bioregulatory genes in general, utilizing IL-2 and IFN-γ as examples. It could not be predicted from this publication that it is the inducibility of the IL-2 gene, and not that of the IFN-γ gene (which has now been found to be normal in BCG-treated patients) would be of clinical importance in connection with superficial bladder carcinoma.

In the course of the study presented herein, the expression of the IL-2 and IFN-γ genes, induced by phytohemagglutinin (PHA) in PBMC from patients with superficial bladder carcinoma undergoing a course of treatment with BCG has been analyzed. As will be shown herein below, inducibility of IL-2 gene at the time of treatment is a powerful predictive indicator of remission, while lack of inducibility of the IL-2 gene is predictive of relapse or persistence of the tumor. The extent of this expression can therefore be used as the desired diagnostic tool described above.

SUMMARY OF THE INVENTION AND ADVANTAGES

According to the present invention, a method for the prediction of the response of a patient suffering from superficial bladder carcinoma to treatment with bacillus Calmette-Guérin (BCG) is provided. The method calculates the inducibility of the Interleukin-2 gene of the patient. Peripheral blood mononuclear cells are obtained from the patient during the course of treatment of the patient with BCG. The sample is divided into at least two aliquots where the cells in a first aliquot are cultured in the presence of an inducing agent for inducing expression of the IL-2 gene and the cells in the second aliquot are cultured in the absence of the inducing agent. The cells in each aliquot are cultured, and then the extent of expression of the IL-2 gene is quantitatively determined for each aliquot. The ratio of the extent of the expression of the IL-2 gene in the first aliquot to the extent of the expression of the IL-2 gene in the second aliquot is calculated, the ratio providing a measure of the inducibility of the IL-2 gene. The inducibility has a direct relationship with the probability of entering remission, relapse or persistence of bladder carcinoma in the patient.

The invention further provides a method of improving the response of a patient suffering from superficial bladder carcinoma to treatment with BCG by calculating the inducibility of the Interleukin-2 gene of the patient in a sample of peripheral blood mononuclear cells from the patient by the method described above. Where the inducibility is absent or low, the patient is treated with either a cytokine preparation, a second course of BCG, or with a second course of BCG in combination with a cytokine preparation.

In a further aspect, the invention relates to a kit for determining the inducibility ratio.

BRIEF DESCRIPTION OF THE DRAWINGS

Other advantages of the present invention will be readily appreciated as the same becomes better understood by reference to the following detailed description when considered in connection with the accompanying drawings wherein:

FIG. 4 is a bar graph showing inducibility of the IFN-γ gene as a function of duration of treatment with BCG wherein induced expression of IFN-γ mRNA in culture conditions k–m (see description of FIG. 1) is shown for a bladder carcinoma patient's PBMC, taken just before each of six successive weekly treatments with BCG, Quantitation was as for FIGS. 1–3;

FIGS. 5A–B are two bar graphs showing analysis of inducibility of IL-2 and IFN-γ mRNA as a function of remission and of relapse or persistence of the tumor wherein PBMC were isolated from 73 patients with superficial bladder carcinoma undergoing treatment with BCG and after culture as for FIG. 1 in conditions k–m, mRNA was quantitated, the index of induction (l/k) and (m/k) were determined for each patient, median values of index of induction, calculated separately for the group that entered remission (n=50) and the group that had relapse or persistence of the tumor (relapse)(n=23), are shown in (A) for IL-2 mRNA and in (B) for IFN-γ mRNA;

DETAILED DESCRIPTION OF THE PREFERRED EMBODIMENT

Figure 1A:
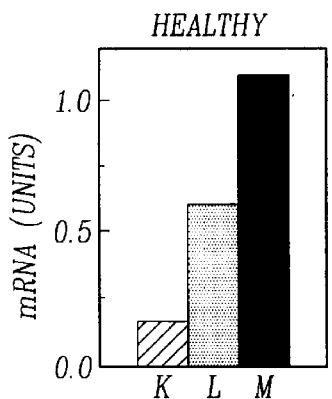
FIGS. 1A–F are a series of bar graphs showing induction of IL-2 and IFN-γ mRNA in PBMC from representative patients with superficial bladder carcinoma preceding remission (B, E) or relapse (C, F) and from a healthy donor (A, D), PBMC were isolated from a healthy donor [Gerez et al. (1991a); Gerez et al. (1991b)] that received no treatment at all and, before the fourth treatment with BCG, from a patient that responded with remission and one that subsequently had relapse, Cells were cultured (k) for 18 hours in the absence of inducer, (l) for 18 hours with PHA and (m) for 22 hours with PHA before IL-2 mRNA (A–C) and IFN-γ mRNA (D–F) were quantitated by hybridization analysis.
Figure 1B:
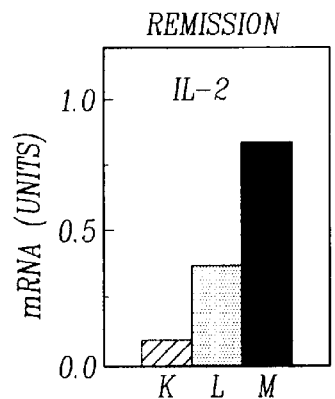
Figure 1C:
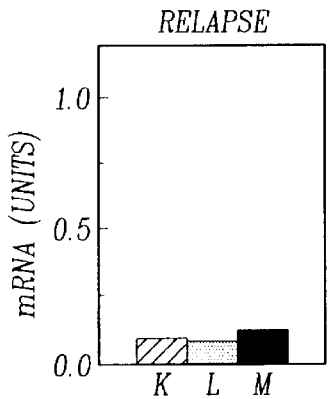
Figure 1D:
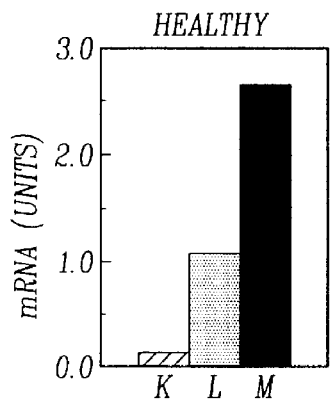
Figure 1E:
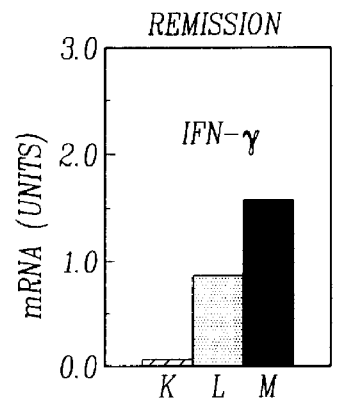
Figure 1F:
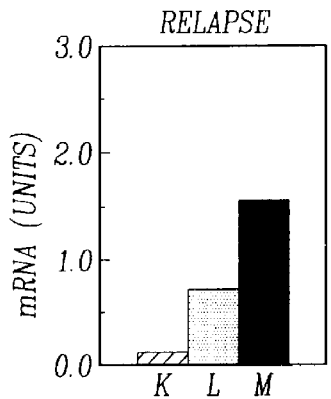

Superficial bladder carcinoma, treated by resection and intravesical administration of bacillus Calmette-Guérin (BCG), yields a remission rate approaching 70%. The present invention relates to a method which enables the prediction of the response of a patient suffering from superficial bladder carcinoma to treatment with BCG. Such prediction would make it possible to give patients with poor prospects of remission repeated, alternative or complementary treatment, improving the probability of survival.

In good agreement with earlier reports [Herr, et. al. (1983); Lamm, et. al. (1980b); Brosman, (1982b)], treatment of superficial bladder carcinoma with BCG in the study of 73 patients described in the following Examples, led to an overall remission rate of 68%, while 32% of the patients had relapse or persistence of the tumor. Previously, the result of treatment could not be predicted with greater precision. As shown herein, inducibility of the IL-2 gene, determined in the course of treatment with BCG, can serve as a powerful predictive indicator of the subsequent response of the patient and of clinical outcome. Patients showing inducibility of the IL-2 gene have a 97% probability of entering remission while those exhibiting a lack of inducibility have a 60% probability of relapse or persistence of the tumor (78% for patients with CIS). This is an unexpected result. These high predictive values support the diagnostic utility of analysis of induced expression of the IL-2 gene.

Determination of induction of IL-2 gene expression in a patient's PBMC, as described herein, is able to provide feedback on the response of the patient even before termination of treatment. Patients showing a lack of inducibility of the IL-2 gene can receive extended, complementary or alternative treatment well before tumors recur.

Thus, the present invention relates to a method for the prediction of the response of a patient suffering from superficial bladder carcinoma to treatment with BCG, by calculation the inducibility of the IL-2 gene of the patient in a sample of peripheral mononuclear cells from the patient, comprising the steps of:

(a) Dividing a peripheral blood sample from a patient in the course of treatment of the patient with BCG into at least two aliquots.

(b) Culturing the cells in each aliquot obtained in step (a) wherein the cells in a first aliquot are cultured in the presence of an inducing agent for inducing expression of the IL-2 gene and the cells in the second aliquot are cultured in the absence of the inducing agent.

(c) quantitatively determining the extent (amount) of expression of the IL-2 gene. The ratio of the extent of the expression of the IL-2 gene in the first aliquot to the extent of the expression of the IL-2 gene in the second aliquot is calculated, the ratio providing a measure of the inducibility of the IL-2 gene. The inducibility is in direct relationship with the probability of entering remission, relapse or persistence of bladder carcinoma in the patient.

In a preferred embodiment the RNA specific for the IL-2 gene generated in an induced culture/aliquot, and thereby for the extent of IL-2 gene expression, is isolated and quantitated utilizing the method as set forth in EPO 0309558 incorporated in its entirety herein by reference. Briefly, in this method RNA is isolated from each aliquot by lysing each of the cell cultures/aliquots by the addition of a suitable lysing agent. Each of the lysates is then homogenized and subsequently the RNA in each of the lysates is selectively precipitated by a suitable precipitating agent. In embodiments of the invention the lysing agents can be guanidinium-hydrochloride or guanidinium thiocyanate. Preferred precipitating agents can be sodium or potassium acetate or absolute ethanol. Specific inducing agents can be phytohemagglutinin (PHA) or concanavalin A (ConA).

In this embodiment the RNA is quantitated in each aliquot by blotting the RNA isolated from each aliquot onto a support matrix. Each of the blotted RNA samples is then hybridized with a labeled riboprobe specific to the IL-2 gene. The extent of binding of the labeled riboprobe to the blotted RNA is then determined.

Alternative methods known in the art to determine the extent (amount) of specific gene expression can be used. Additionally, alternative methods known in the art to isolate and determine the amount of a specific RNA in each sample can be used.

According to the method of the invention BCG is administered to the patient repeatedly and at least one peripheral blood sample is collected at a suitable time in the course of the repeated administrations of BCG. In the Examples described hereinafter, the BCG was administered to the patient on a weekly basis and the peripheral blood samples were preferably collected before the third and/or fourth weeks of administration of BCG, since even where inducibility of the IL-2 gene was found at the onset of treatment, it had increased significantly by the third and fourth weeks. Two blood samples may be collected for sake of safety, in case the determination is miscarried or lost.

In a second aspect, the invention relates to methods for improving the response of a patient suffering from superficial bladder carcinoma to treatment. Using the prediction method of the invention, the ratio of the extent of the expression of the IL-2 gene in the first aliquot to the extent of the expression of the IL-2 gene in the second aliquot is calculated. In case the ratio calculated is below about 1.5, the patient can be given treatment with a cytokine preparation, by administering to the patient a suitable cytokine preparation. The cytokine preparations can be recombinant or natural cell products. A preferred cytokine preparation is a recombinant IL-2 preparation.

Alternatively, when the ratio is below about 1.5, the patient may be administered a second course of treatment with BCG. In accepted current practice, patients are sometimes subjected to further treatment or treatments with BCG, in case of relapse. The method of the present invention enables such subsequent treatment well before tumors recur.

Still alternatively, a subsequent course of treatment with BCG may be combined with treatment with a cytokine preparation, preferably a recombinant IL-2 preparation.

The alternative treatment course are utilized and administered in the present invention consistent with good medical practice. The treatment course is selected in accordance with good medical practice taking into account the clinical condition of the individual patient and other factors known to medical practitioners skilled in the treatment of bladder cancer.

Patients with papillary tumors are subjected to surgery before BCG treatment. Efficacy of tumor removal may be a determining factor for remission. Within the group of patients that did not show inducibility of IL-2 mRNA, yet responded to treatment (40% of non-inducible cases), 13/15 had papillary tumors. It should be considered that transurethral resection by itself cures papillary tumors without any recurrences in about 40% of cases [Shapiro, et al. (1982)].

Therefore, it is still to be expected that about 40% of the subgroup that did not exhibit inducibility will be cured by transurethral resection alone.

Patients with CIS, by contrast, are treated only with repeated doses of BCG. Remission in CIS patients, therefore, can be attributed entirely to treatment with BCG. It is thus important to note that 86% of patients with CIS showing inducibility of IL-2 mRNA entered remission, while 88% of those showing lack of inducibility had relapse or persistence of the tumor.

Applicants measured the transient expression of IL-2 and IFN-γ mRNA in PBMC from patients. Determination of mRNA gives dynamic information on the primary response of these genes within hours after their induction. By analyzing both genes, any anomaly in expression is detected with greater sensitivity. During an immune stimulus, production of IL-2 is restricted to the Th1 subset of CD4-positive helper T cells. [Mosmann, et al. (1986)].

IFN-γ is likewise expressed primarily by Th1 cells, though natural killer cells and large granular lymphocytes are also able to produce this cytokine. [Bancroft, et al. (1989); Bancroft, et al. (1992)]. IL-2 and IFN-γ are considered to be Th1-type cytokines, in contrast to IL-4 and IL-10 which are expressed in the Th2 subpopulation. [Mosmann, et al. (1986); Mosmann, et al. (1989)]. The present data show that inducibility of IL-2 mRNA has high predictive value, yet inducibility of IFN-γ mRNA does not show a significant correlation with response to treatment with BCG. This result strongly suggests that lack of inducibility of IL-2 mRNA in PBMC from BCG-treated patients with superficial bladder carcinoma is not associated with a general lack of Th1 function but instead, reflects a more specific impairment.

It is clear that determination of the inducibility of the IFN-γ gene would not have any predictive value, in connection with superficial bladder carcinoma. The present results show that disease-free interval increases in a highly significant manner with inducibility of IL-2 mRNA (p=0.0001). Expression of the patient's own IL-2 gene is apparently essential for mounting an anti-tumor response during superficial bladder carcinoma. In a murine model, regression of bladder tumors could be observed upon treatment with a cell line expressing the IL-2 gene [Connor, et al. (1993)]. However, this publication relates to the effect of exogenous IL-2, secreted from bladder tumor cells implanted into mice that were not treated with BCG or any other immunostimulating agent. This publication would not have motivated a person skilled in the art to analyze the pattern of expression of the patient's own IL-2 gene and employ the same as a tool for predicting the response of that patient to BCG.

Inducibility of IL-2 mRNA is an independent prognostic parameter and useful predictive indicator of remission vs. relapse. Because inducibility of IL-2 mRNA differs in a significant manner for patients who will stay in remission and for those who will suffer relapse or persistence of the tumor, this parameter can serve as a diagnostic tool to identify patients likely to have future relapse or persistence of the tumor, thus allowing them to receive a further treatment well before relapse or persistence of the tumor can be detected. This combination of the diagnostic results obtained by the method of the invention, with, where necessary, additional treatment improving the probability of remission, is one of the major advantages of the present invention.

In a third aspect, the invention relates to a diagnostic kit for the prediction of the response of a patient suffering from superficial bladder carcinoma to treatment with BCG, by calculating the inducibility of the IL-2 gene of the patient in a sample of peripheral blood mononuclear cells from the patient. The diagnostic kit of the invention comprises an inducing agent and reagents for RNA isolation. In a preferred embodiment the reagents for RNA isolation comprise a lysing agent, a precipitating agent, a prehybridization buffer and a riboprobe, specific to the gene of interest the IL-2 gene and are included. The kit may include additional conventional reagents and/or devices, required for carrying out the inducibility tests. The inducing agent, lysing agent, and precipitating agent are generally in an aqueous buffered solution but can be supplied in any suitable form. The inducing agent can be PHA or concanavalin A. The lysing agent can be guanidinium-hydrochloride or guanidinium thiocyanate. The precipitating agent can be sodium or potassium acetate or absolute ethanol.

The above discussion provides a factual basis for the method of predicting the response of a patient suffering from superficial bladder carcinoma to treatment with BCG. The methods used with and the utility of the present invention can be shown by the following examples.

EXAMPLES

PATIENTS AND METHODS:

Patients:

Samples of peripheral blood were obtained from patients with superficial bladder carcinoma treated at the Hadassah University Hospital as part of routine kidney, liver and blood function tests. Diagnosis was made following an intravenous pyelogram, cytologic analysis of urine, cystoscopy and examination under anesthesia. Patients with papillary tumors were first subjected to surgery to remove any visible tumor; multiple random bladder biopsies were taken. A second group of patients had flat, anaplastic superficial tumors diagnosed by multiple biopsies (CIS). For both CIS and stage A high grade tumors, a computerized tomography scan of lungs, abdomen and pelvis was performed. For stage 0 papillary tumors, no further assessment was made.

Both groups of patients were treated with BCG starting 7–10 days after diagnosis. Treatment consisted of six weekly repeated, intravesical administrations of BCG, using either 150 mg of fresh, living bacteria (Pasteur Institute, France) or 120 mg of freeze-dried bacteria (Connaught, Canada) in 50 ml of 0.9% NaCl, introduced into the bladder through a urethral catheter which was removed. The mixture was kept in the bladder for 2 hours. All patients displayed signs of urinary tract infections (urgency, frequency, dysuria) but none had lung or liver infections with BCG.

Evaluation and Follow-Up:

Remission was defined by negative cytology and cystoscopy and, for patients with CIS, also by biopsies. Relapse or persistence of the tumor was defined by positive cytology, cystoscopy or biopsy examinations. These examinations were performed every three months during the first year after the start of treatment, every four months during the second year and every six months thereafter. Median duration of follow-up was 24 months (range, 3–48 months). Median follow-up for remission cases was 36 months; follow-up was for $\geq 24$ months, except in two cases of death from unrelated causes after six and nine months, respectively.

Cell Culture and induction of Gene Expression:

Before both the third and fourth administrations of BCG, 10 ml of peripheral blood was collected for analysis of gene expression. Generally, gene expression patterns at the fourth week of treatment were used for analysis, except in 12 cases where only the pattern from the third treatment was available.

PBMC were collected by standard methods, washed and suspended at a density of $0.5–4 \times 10^6$ cells/ml in 3 ml of culture medium containing 2% fetal calf serum [Arad, et al. (1995); Gerez, et al. (1991a)]. For each subject, 1-ml cell cultures were incubated: (k) for 18 hours in the absence of inducer; (l) for 18 hours with PHA (0.4% PHA-P, Difco); and (m) for 22 hours with PHA.

Plasmids and Hybridization Probes:

Human IL-2 and IFN-γ complementary DNA were placed under the phage T7 promoter in pGEM-3 (Promega) to generate anti-sense RNA transcripts labeled with $[\alpha\text{-}^{32}P]$ ATP [Gerez, et al. (1991a); Gerez, et al. (1991b)]. In total RNA isolated from lymphocytes induced with PHA, [Arad, et al. (1995)] IL-2 and IFN-γ anti-sense RNA transcripts hybridize to RNA species migrating at 1,000 and 1,300 nucleotides, respectively, as expected for mRNA, comprising over 85% of the total hybridization signal; remaining hybridization is to larger precursor transcripts. Sense RNA, generated from the SP6 promoter, gave no detectable hybridization.

Quantitation of Specific mRNA:

Cells from each culture were collected and lysed in 7.5M guanidinium-HCl [Cheley, et al. (1984)]. RNA, precipitated over-night in ethanol at $-20°$ C., was dissolved into formaldehyde and incubated for 15 minutes at $60°$ C. Eight serial 2-fold dilutions, made in 10× saline sodium citrate, were applied in duplicate to nitrocellulose sheets, using a 96-well dot blot apparatus. After baking in a vacuum oven, sheets were hybridized separately with $^{32}$P-labeled RNA probes for IL-2 and IFN-γ. Each hybridization included a strip of nitrocellulose containing serially diluted standard RNA, purified from human tonsil cells induced with PHA for 24 hours [Efrat, et al. (1982); Gerez, et al. (1991a); Gerez, et al. (1991b)]. Exposed autoradiograms were scanned at 630 nm in an ELISA reader.

Statistical Analysis:

All group comparisons were made using the nonparametric Wilcoxon test [see Sokal R. R., Rohlf F. J., Biometry. 2nd ed. New York: W. H. Freeman and Co., (1981)]. Multivariate logistic analysis was applied to the log-transformed values of IL-2 and IFN-γ mRNA, to examine their discrimination power [see Cornell R., Statistical methods for cancer studies. New York: M. Dekker, Inc., (1984)]. Significance values in a 2×3 table were determined by the Mantel-Haenszel test for linear trend [see Mantel N. and Haenszel, W., J Amer Statistical Assn 22:719–748 (1959)]. Disease-free interval curves were calculated using the Kaplan-Meier method [see Harris E. K. and Albert A., Survivorship analysis for clinical studies. New York: M. Dekker, Inc., (1991)].

RESULTS

During BCG treatment, applicants analyzed induction of IL-2 and IFN-γ mRNA in PBMC from 73 patients, 51 with papillary tumors and 22 with carcinoma in situ (CIS). Results were correlated with remission, relapse or tumor persistence over a 4-year follow-up.

Independent of tumor type, induction of IL-2 mRNA was observed for patients that responded with remission but not for those suffering relapse (p=0.0001). Multivariate logistic analysis showed that inducibility of IL-2 mRNA is the discriminating parameter, yielding a predictive value of 97% for remission. Out of 23 patients suffering relapse/persistence, 22 lacked inducibility of IL-2 mRNA, a sensitivity of 95.6%, while 35/50 patients in remission exhibited inducibility, a specificity of 70%. For patients with carcinoma in situ, where remission or failure depends solely on response to BCG, sensitivity and specificity were 88% and 86%, respectively; for patients with papillary tumors, they were 100% and 64%. IFN-γ mRNA, by contrast, was clearly inducible in PBMC from all patients (p=0.51). Disease-free interval increased progressively with inducibility of IL-2 mRNA; this trend was highly significant (p=0.0001).

Induction of IL-2 and IFN-γ mRNA

A total of 73 patients with superficial bladder carcinoma, 51 with papillary tumors and 22 with CIS, was analyzed. Most of the patients were men (86%) and the median age was 68 years. All patients were treated with BCG. Relapse or persistence of the tumor was observed in 32% of the patients (23/73), in 29% of those with papillary tumors (15/51) and in 36% of those with CIS (8/22); overall remission rate was 68%.

FIG. 1 shows patterns of induction of IL-2 and IFN-γ mRNA for three representative, individual subjects: a healthy donor, a case that responded with remission and a case that had relapse. Gene expression patterns were determined for the superficial bladder carcinoma patients during treatment with BCG, just before the fourth administration. mRNA levels were measured at 18 and 22 hours after induction with PHA; usually, the 22 hours point was higher (cf. l and m in FIG. 1). Both IL-2 and IFN-γ genes were inducible in the healthy donor and in the patient that went into remission. By contrast, IFN-γ mRNA, but not IL-2 mRNA, was inducible in the patient that had relapse.

Figure 3:
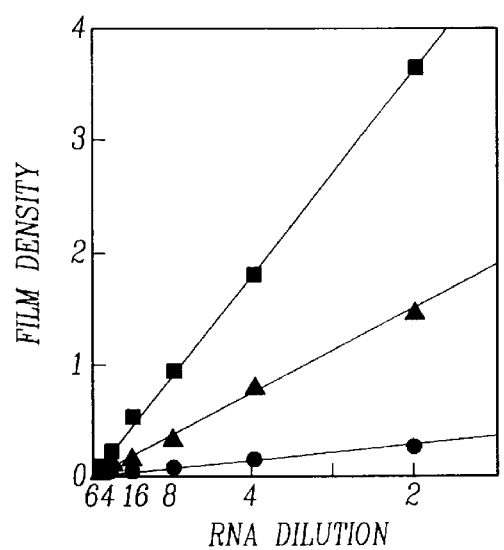
FIG. 3 is a graph showing the linearity of the hybridization response, wherein hybridization intensity of IL-2 mRNA was quantitated for the autoradiogram of FIG. 2B by microdensitometry at 630 nm, Data shown are for culture conditions k (●, linear regression coefficient R=0.999), l (▲, R=0.992) and m (■, R=0.999)
Figure 2A:
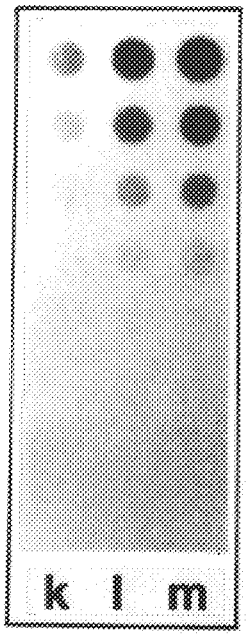
FIGS. 2A–F are a series of photographs of autoradiography results showing hybridization intensity of IL-2 and IFN-γ mRNA in PBMC from representative patients with superficial bladder carcinoma preceding remission or relapse and from a healthy donor, wherein autoradiograms of IL-2 (A–C) and IFN-γ mRNA (D–F) were used to generate the data shown in panels A–F in FIG. 1, horizontal rows show film density in culture conditions k, l and m (see FIG. 1); from top to bottom, columns show eight serial twofold dilutions of RNA, each hybridization included the same RNA standard (not shown), Exposure time was more prolonged for (C)
Figure 2B:
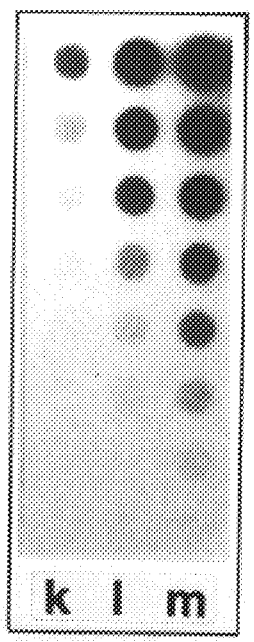
Figure 2C:
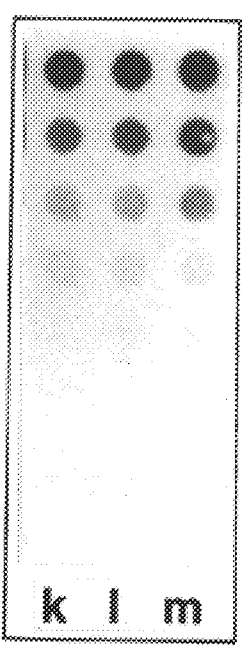
Figure 2D:
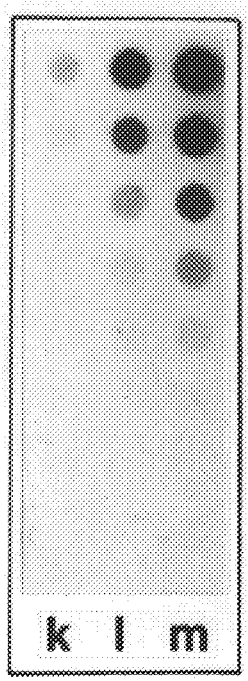
Figure 2E:
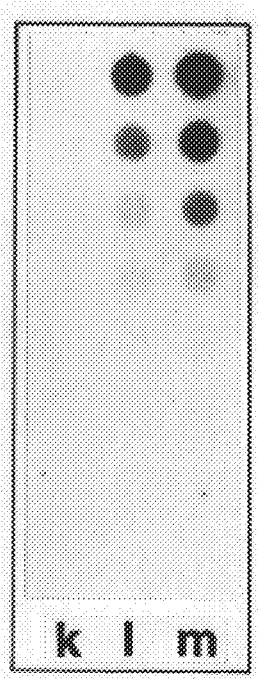
Figure 2F:
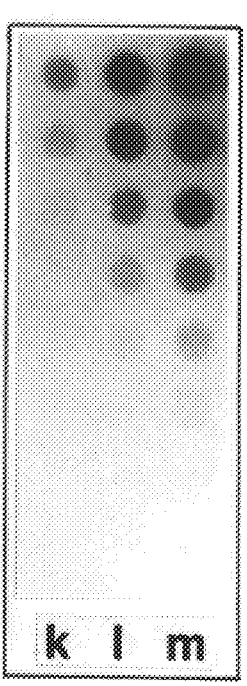
Figure 6A:
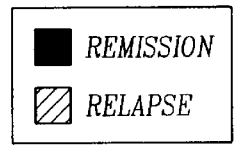
FIGS. 6A–D are a series of bar graphs showing analysis of inducibility of IL-2 and IFN-γ mRNA in patients with carcinoma in situ (CIS) or papillary tumors as a function of remission and of relapse or persistence of the tumor wherein PBMC were isolated from 22 patients with CIS (A, C) and 51 with papillary tumors (B, D) undergoing treatment with BCG and after culture as for FIG. 1 in conditions k–m, mRNA was quantitated, the index of induction (l/k) and (m/k) were determined for each patient, median values of index of induction, calculated separately for the group that entered remission and the group that had relapse or persistence of the tumor (relapse), are shown for IL-2 mRNA (A, B) and IFN-γ mRNA (C, D)
Figure 6A:
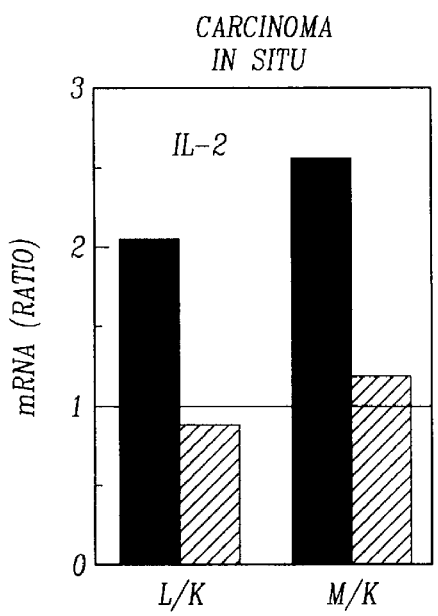
Figure 6B:
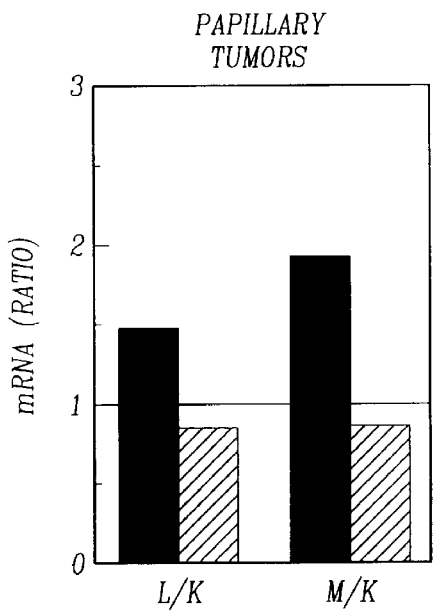
Figure 6C:
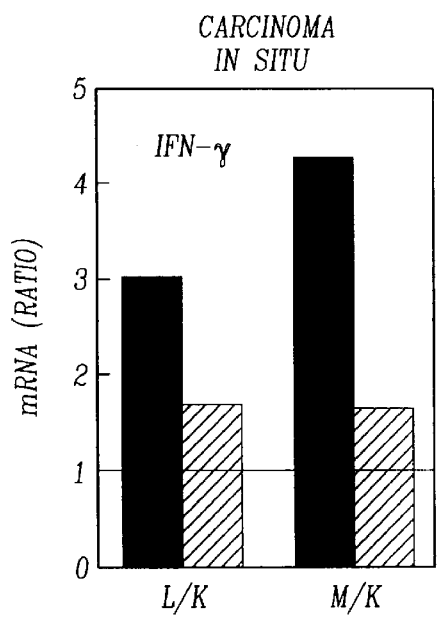
Figure 6D:
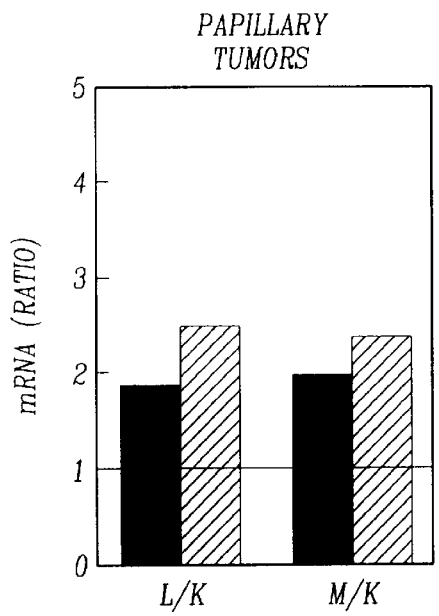

Autoradiograms of the hybridization analyses used to quantitate expression of IL-2 and IFN-γ mRNA in PBMC from these patients are shown in FIG. 2. For each dilution series, hybridization intensities, expressed in $A_{630}$, were subjected to linear regression analysis. The slope is proportional to mRNA concentration (FIG. 3). Hybridization intensity is linear not only with amount of RNA (FIG. 3) but also with number of PBMC [Gerez, et al. (1991a)] and can be quantitated accurately over two orders of magnitude [Gerez, et al. (1991a)]. Taking cell density during induction into account, this value is expressed as standard units of mRNA/cell, allowing direct comparison of results from individual patients [Gerez, et al. (1991a); Gerez, et al. (1991b)]. Levels of IFN-γ and IL-2 mRNA quantitated by this method consistently reflect amounts of specific mRNA as determined, in controls that included a β-actin marker, by ribonuclease protection analysis or by blot hybridization of total cellular RNA subjected to agarose gel electrophoresis [Shaw, et al. (1988); Arad, et al. (1995)]. For 11 patients with superficial bladder carcinoma, PHA-induced expression of IL-2 and IFN-γ mRNA was determined in PBMC taken before each of 6 successive weekly treatments with BCG.

A representative pattern of expression is illustrated for IFN-γ mRNA in FIG. 4. Inducibility was found at the onset of treatment, but by weeks 3 and 4, it had increased significantly. Where the IL-2 gene was expressed, it followed a similar pattern. Thus, for this set of patients, of whom 6/11 had subsequent relapse, inducibility, expressed as m/k, increased between weeks 1 and 3 by a factor of 2.40±0.84 for IL-2 mRNA and by 3.05±1.49 for IFN-γ mRNA. Generally, inducibility receded by week 6 of treatment. For these reasons, for an additional 62 bladder carcinoma patients, gene expression patterns were determined only before the third and fourth administrations of BCG. The basis for the changes in degree of inducibility in the course of BCG treatment of bladder carcinoma patients is not yet understood.

Log-transformed values of k, l and m for IL-2 and IFN-γ mRNA showed nearly symmetrical, unimodal distributions when analyzed for all patients, for the group that entered remission or for the group that had relapse or persistence of the tumor and were used for analysis of the extent of induction of IL-2 and IFN-γ genes. mRNA inducibility, defined as the ratio of mRNA expressed upon culture of PBMC with the inducer (see l, m in FIG. 1) and in its absence (k in FIG. 1), was analyzed individually for each of the 73 patients. Patients that responded with remission showed inducibility of IL-2 mRNA at the time of treatment with BCG, manifested by median values of l/k and m/k>1 after 18 and 22 hours of induction, respectively, but patients that had subsequent relapse or persistence of the tumor showed no inducibility (FIG. 5A)(p=0.0001 for l/k; p=0.0001 for m/k). IFN-γ mRNA, by contrast, was clearly inducible in both groups of patients (FIG. 5B)(p=0.78 for l/k; p=0.51 for m/k).

mRNA Inducibility in Patients with CIS or Papillary Tumors

In FIG. 6, inducibility of IL-2 and IFN-γ mRNA at the time of BCG treatment is analyzed separately for patients with CIS and for those with papillary tumors. Independently of the nature of the tumor, induction of IL-2 mRNA was observed for patients that responded with remission but not for those that were to have relapse or persistence of the tumor (FIGS. 6A,B)(CIS: p=0.022 for l/k and p=0.003 for m/k; papillary tumors: p=0.001 for l/k and p=0.0001 for m/k). Even though median values of index of induction of IL-2 mRNA, in FIGS. 2 and 3 remain within the range of 0.8–3, they yield a highly significant correlation with response to treatment.

Patients with papillary tumors exhibited similar inducibility of IFN-γ mRNA whether they entered remission or had relapse or persistence of the tumor (FIG. 6D) (p=0.27 for l/k and p=0.78 for m/k). For CIS patients, inducibility of IFN-γ mRNA was higher for those that had subsequent remission than for those that had relapse or persistence of the tumor (FIG. 6C) but this difference was not significant (p=0.34 for l/k and p=0.18 for m/k). However, IFN-γ mRNA was clearly inducible even in those CIS patients that had relapse or persistence of the tumor (p=0.08 for l; p=0.02 for m).

Prediction of Response to Treatment Through IL-2 Gene Expression

It was seen that out of a total of six measurements for induction of IL-2 and IFN-γ gene expression, values k, l and m for IL-2 mRNA can be used to distinguish between the patient populations according to clinical outcome, relapse/persistence of the tumor or remission. Measurements of IFN-γ mRNA showed in part a similar trend but failed to achieve significance. In FIGS. 5 and 6, only two measurements were examined at a time.

To study if greater resolution of the two populations could be achieved by utilizing more parameters, a multivariate logistic model was applied to the data. This model included as the dependent variable whether a patient responded or not, and all of the above 12 measurements as covariates. Stepwise logistic regression led to a model containing only the parameters k and m for the IL-2 gene. The estimated coefficients of k and m were almost equal in absolute value (2.16 and −1.97, respectively), suggesting a model of their difference (m−k) or, when transformed back from the log to the original scale, a model of one parameter, the ratio m/k. Indeed, when multivariate logistic analysis was applied to this parameter only, it resulted in an equivalent model in terms of goodness of fit criteria, showing that the parameter discriminating between the two populations is the induction ratio m/k for IL-2 mRNA.

Figure 7A:
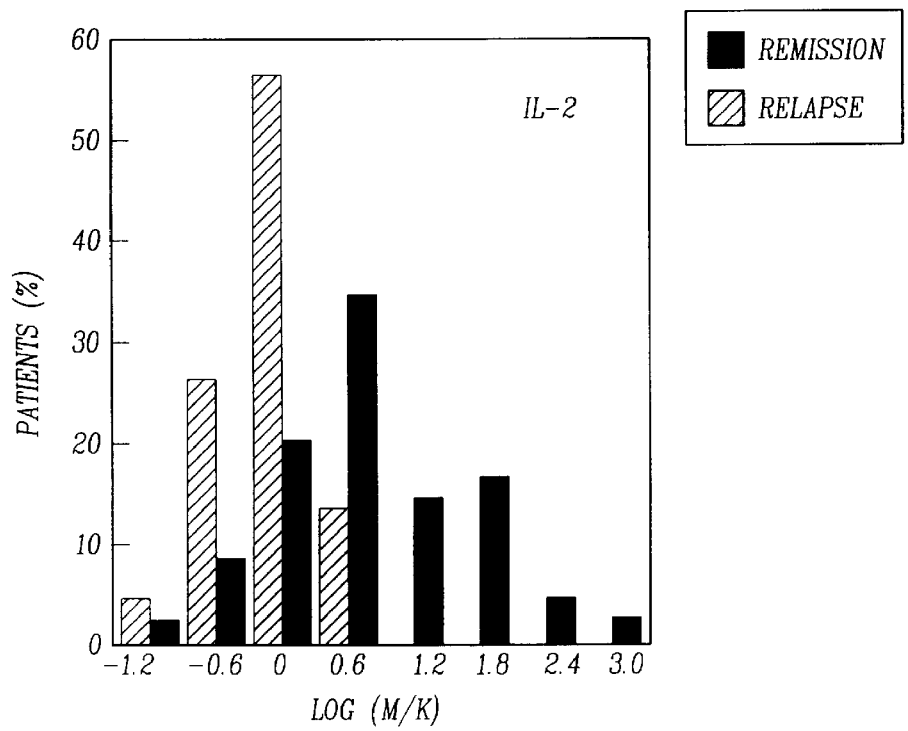
FIGS. 7A–B are two bar graphs showing distribution of remission or relapse in patients with superficial bladder carcinoma as a function of inducibility of IL-2 and IFN-γ mRNA at time of treatment with BCG wherein Percentage of 73 patients that entered remission or had relapse or persistence of the tumor (relapse) subsequent to treatment with BCG is plotted as a function of inducibility of IL-2 mRNA (A) and IFN-γ mRNA (B) in their PBMC, expressed as log (m/k) (see description of FIG. 5)
Figure 7B:
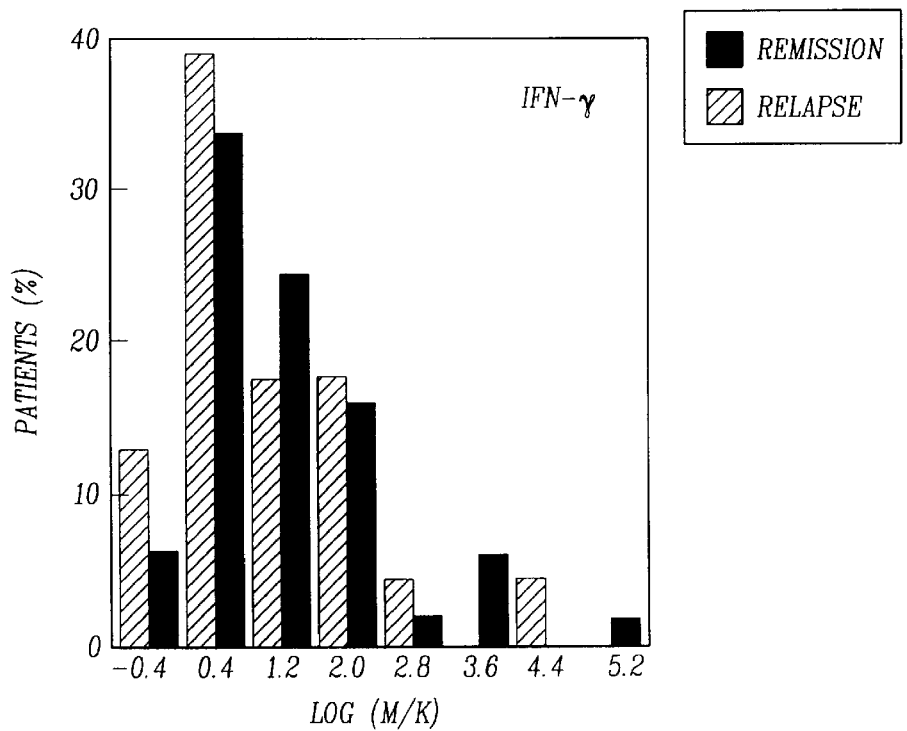

In FIG. 7, the distribution of remission or relapse in 73 patients with superficial bladder carcinoma is plotted as a function of the inducibility of IL-2 and IFN-γ mRNA in their PBMC at the time of treatment with BCG. Inducibility of IL-2 mRNA, expressed as log (m/k), exhibits a relatively smooth unimodal distribution for both groups but is clearly shifted towards higher values for patients that will enter remission (FIG. 7A). Inducibility of IFN-γ mRNA, by contrast, yields two overlapping distributions that fail to discriminate between the two populations (FIG. 7B).

To further examine the discriminating power of the induction ratio m/k for IL-2 mRNA, the 73 patients with superficial bladder carcinoma were divided into three equal groups, according to highest (n=24), medium (n=25) and lowest (n=24) values of m/k. For the group with high m/k values, 100% remained disease-free during 30 months of follow-up, compared to 68% for the group with medium values and 38% for patients with low values (p<0.001).

Figure 8:
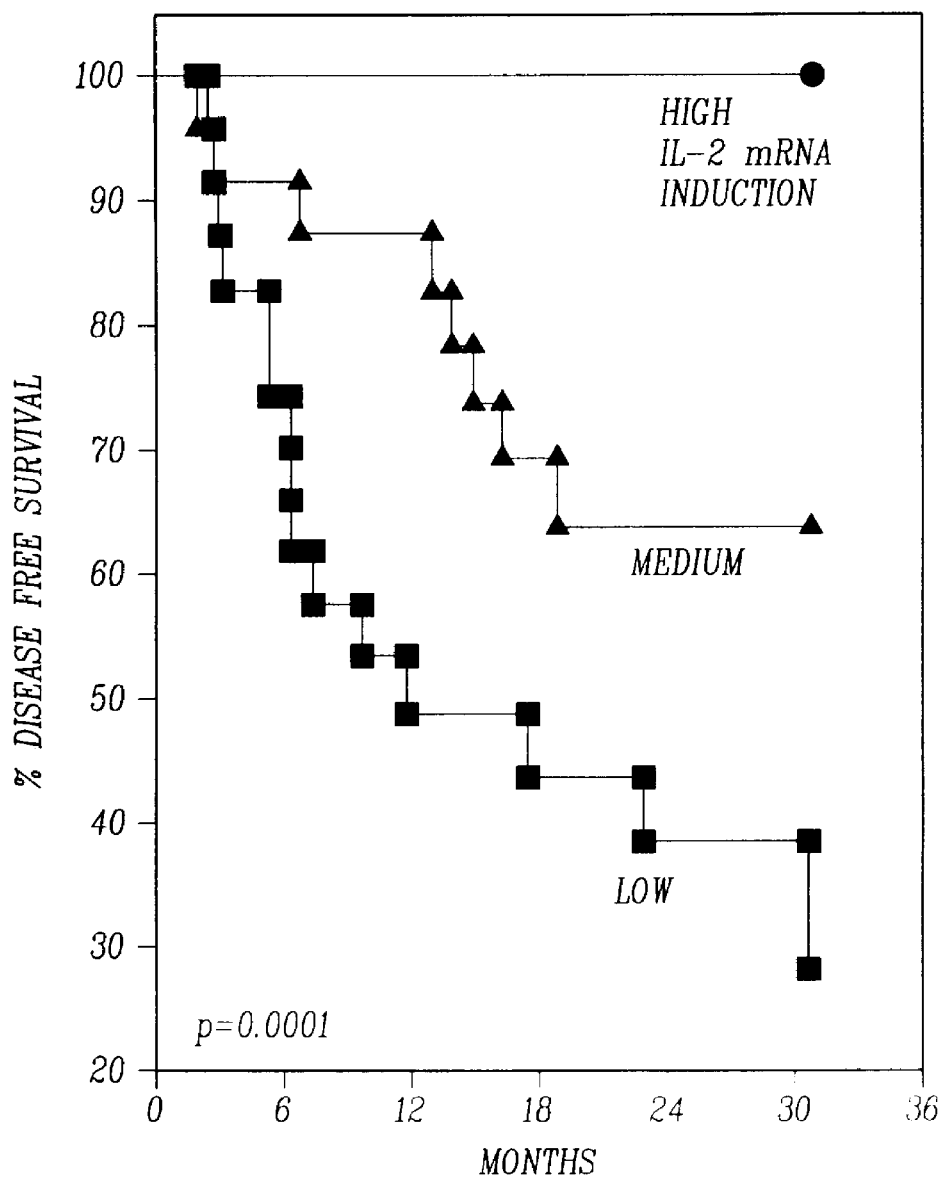
FIG. 8 is a bar graph showing disease-free interval as a function of inducibility of IL-2 mRNA wherein the 73 patients with superficial bladder carcinoma in this study were divided into 3 equal groups, according to highest (n=24), medium (n=25) or lowest values (n=24) of induction ratio m/k for IL-2 mRNA.

FIG. 8 depicts the disease-free interval, defined as the time elapsed between start of BCG treatment and relapse, for each of the three groups. Disease-free interval is seen to increase progressively and unequivocally with increasing inducibility of IL-2 mRNA (p=0.0001).

The median of the induction ratio m/k for IL-2 mRNA was 1.5. Applicants examined the results in terms of a dichotomic partition using this median value as cutoff point. Out of 36 patients (49.3%) with induction ratio m/k for IL-2 mRNA ≧1.5 (induction of 50% or more), only 1 (2.8%) had relapse, yielding a predictive value of 97% for remission. By contrast, out of 37 patients (50.7%) with m/k<1.5, 22 (59.5%) suffered relapse. Starting from disease status, 22/23 relapse patients showed an induction ratio for IL-2 mRNA <1.5, yielding a sensitivity value of 95.6%, while 35/50 patients in remission showed an induction ratio ≧1.5, yielding a specificity value of 70%.

The above 50% induction rule was also applied separately to data for the subgroups of patients with CIS and with papillary tumors. Seven out of eight relapse patients with CIS showed an induction ratio <1.5 for IL-2 mRNA (sensitivity of 88%), while 12/14 CIS patients in remission showed an induction ratio ≧1.5 (specificity of 86%). For patients with papillary tumors, 15 out of 15 relapse patients showed an induction ratio <1.5 for IL-2 mRNA (sensitivity of 100%), while 23/36 patients in remission showed an induction ratio ≧1.5 (specificity of 64%). All patients with papillary tumors that had an induction ratio >1.5 entered remission.

Throughout this application, various publications, including patents, are referenced by citation or number. Full citations for the publications not provided herein above are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

REFERENCES

Arad, G. et al. Cell Immunol 160:240–247 (1995)
Bancroft, G. J. et al. J Immunol 143:127–123 (1989);
Bancroft, G. J. and Schreiber, R. D. Immunol Rev 124:5–24, (1992)
Boccafoschi, C. et al. Eur Urol 21:304–308 (1992)
Bohle, A. et al. J Urol 144:53–58, (1990a)
Bohle, A. et al. J Urology 144:59–64 (1990b)
Bohle, A. et al. Dev Biol Stand 77:199–209 (1992)
Bretton, P. R., et al. J Urol 143:710–712 (1990)
Brosman, S. A. J Urol 143:710–712 (1982a)
Brosman S. A., J. Urol 128:27–30 (1982b)
Bubenik, J. et al. Immunol Lett 18:115–118 (1988)
Cheley, S. et al. Anal Biochem 137:15–19 (1984)
Connor, J. et al. J Exp Med 177:1127–1134 (1993)
Coplen, D. E., et al. J Urol 144:652–657 (1990)
De Jong, W. H. et al. Cancer Immunol Immunother 31:182–186 (1990)
Efrat, S. et al. Nature 297:236–239 (1982)
Efrat, S. et al. Proc Natl Acad Sci USA 81:2601–2605 (1984a)
Efrat, S. et al. Biochem Biophys Res Commun 123:842–848 (1984b)
Gerez L, et al. Clin Immunol Immunopathol 58:251–266 (1991a)
Gerez L, et al. Kidney Int 40:266–272 (1991b)
Gerez, L. et al. J Biol Chem 270:19569–19575 (1995)
Fleischman, J. D. et al. Cancer 64:1447–1454 (1989)
Herr, H. W. et al. Cancer 51:1323–1326 (1983)
Ikemoto, S. et al. Br J Urol 65:333–338 (1990)
Lamm, D. L. et al. Cancer 51:1323–1326 (1980a)
Lamm D. L., et. al. J Urol 142:38–42 (1980b);
Lebendiker, M. A, et al. EMBO J. 6:585–589 (1987)
Mosmann, T. R. et al. J. Immunol 136:2348–2357 (1986)
Mosmann, T. R. et al. Annu Rev Immunol 7:145–173 (1989)
Ratliff, T. L., et al. J Urol 150:1018–1023 (1993)

Shapiro, A. et al. J Urol 128:891–894 (1982)

Shaw, J. et al. Mol Immunol 24:409–419 (1987)

Shaw, J. et al. J. Immunol. 140:2245–2248 (1988)

Silverberg, E. et al. Cancer J Clin 43:18 (1993)

What is claimed is:

1. A method for the prediction of the response of a patient suffering from superficial bladder carcinoma to treatment with bacillus Calmette-Guérin (BCG), by calculating the inducibility of the Interleukin-2 (IL-2) gene of the patient in a sample of peripheral blood mononuclear cells from the patient, comprising the steps of:
   a) dividing at least one peripheral blood sample collected from a patient in the course of treatment of the patient with BCG, at least one week after said treatment, into at least two aliquots;
   b) culturing the cells in each aliquot obtained in step (a) wherein:
      (i) the cells in a first aliquot are cultured in the presence of an inducing agent for inducing expression of the IL-2 gene, and
      (ii) the cells in a second aliquot are cultured in the absence of the inducing agent;
   c) determining quantitatively the extent of expression of the IL-2 gene in each aliquot;
   d) calculating the ratio of the extent of the expression of the IL-2 gene in the first aliquot to the extent of the expression of the IL-2 gene in the second aliquot wherein the ratio is providing a measure of the inducibility of the IL-2 gene wherein
   the inducibility being in direct relationship with the probability of entering remission, relapse or persistence of bladder carcinoma in the patient.

2. The method according to claim 1 wherein said step determining quantitatively the extent of expression of the IL-2 gene in each aliquot is further defining as
   a) isolating RNA from each of the aliquots;
   b) blotting RNA isolated from each aliquot onto a support matrix; and
   c) hybridizing each of the blotted RNA obtained in step (b) with a labeled riboprobe specific to the IL-2 gene.

3. The method according to claim 2 wherein said step isolating RNA is further defining as
   a) lysing each of the cell cultures obtained by the addition a suitable lysing agent;
   b) homogenizing each of the lysates obtained and subsequently selectively precipitating the RNA in each of the lysates by a suitable precipitating agent.

4. The method according to claim 3 wherein the lysing agent is selected from the group consisting of guanidinium-hydrochloride and guanidinium thiocyanate.

5. The method according to claim 3 wherein the precipitating agent is selected from the group consisting of sodium or potassium acetate or absolute ethanol.

6. The method according to claim 1 wherein the inducing agent is selected from the group consisting of phytohemagglutinin (PHA) or concanavalin A.

7. The method according to claim 1 wherein the BCG is administered to the patient repeatedly and the peripheral blood sample(s) are collected at a suitable time in the course of the repeated administrations of BCG.

8. The method according to claim 7 wherein the BCG is administered to the patient on a weekly basis and the peripheral blood sample/s are collected before the third and/or fourth weeks of administration of BCG.

9. A method of improving the response of a patient suffering from superficial bladder carcinoma to treatment with BCG by calculating the inducibility of the IL-2 gene of the patient in a sample of peripheral blood mononuclear cells from the patient by the method according to claim 1 and, in case the ratio is below about 1.5, the patient is subjected to treatment selected from the group consisting of administering to the patient a suitable cytokine preparation, administering to the patient a second course of treatment with BCG, and administering to the patient a second course of treatment with the BCG in combination with a cytokine preparation.

10. A method according to claim 9 wherein the cytokine preparation is recombinant.

11. A method according to claim 9 wherein the cytokine preparation is a natural cell product.

12. A method according to claim 10 wherein the cytokine preparation is recombinant IL-2.

13. A diagnostic kit for the determination of the inducibility of the IL-2 gene in a sample of peripheral blood mononuclear cells from a patient suffering from superficial bladder carcinoma, for use in the prediction of the response of the patient subjected to treatment with bacillus Calmette-Guérin (BCG) comprising:
   an inducing agent; a lysing agent; a precipitating agent; a prehybridization buffer; and a riboprobe, specific to the IL-2 gene; positive control samples comprising a cell sample of peripheral blood mononuclear cells from a patient responsive to treatment with BCG or negative control samples comprising a cell sample of peripheral blood mononuclear cells from a patient nonresponsive to treatment with BCG.

14. A kit according to claim 13 wherein said inducing agent is selected from the group consisting of phytohemagglutinin (PHA) and concanavalin A.

15. A kit according to claim 13 wherein said lysing agent is selected from the group consisting of guanidinium-hydrochloride and guanidinium thiocyanate.

* * * * *